United States Patent
Oftring et al.

(10) Patent No.: US 7,671,234 B2
(45) Date of Patent: Mar. 2, 2010

(54) METHOD FOR PRODUCING METHYLGLYCINE-N,N-DIETHANOIC ACID-TRIALKALI METAL SALTS WITH A LOW BY-PRODUCT CONTENT

(75) Inventors: Alfred Oftring, Bad Duerkheim (DE); Gerold Braun, Ludwigshafen (DE); Friedrich Wirsing, Kaiserslautern (DE); Armin Stamm, Nieder-Olm (DE); Kai-Uwe Baldenius, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/913,597

(22) PCT Filed: May 2, 2006

(86) PCT No.: PCT/EP2006/061968

§ 371 (c)(1),
(2), (4) Date: Apr. 23, 2008

(87) PCT Pub. No.: WO2006/120129

PCT Pub. Date: Nov. 16, 2006

(65) Prior Publication Data

US 2008/0194873 A1  Aug. 14, 2008

(30) Foreign Application Priority Data

May 6, 2005  (DE) .................. 10 2005 021 055

(51) Int. Cl.
*C07C 227/26* (2006.01)
*C07C 229/16* (2006.01)

(52) U.S. Cl. ..................................... 562/571

(58) Field of Classification Search .................. None
See application file for complete search history.

(56) References Cited

U.S. PATENT DOCUMENTS 5,849,950 A    12/1998    Greindl et al.

FOREIGN PATENT DOCUMENTS

WO    94/29421    12/1994

*Primary Examiner*—Paul A Zucker
*Assistant Examiner*—Yevegeny Valenrod
(74) *Attorney, Agent, or Firm*—Oblon, Spivak, McClelland, Maier & Neustadt, L.L.P.

(57) ABSTRACT

The invention relates to a process for preparing low-by-product, light-color methylglycine-N,N-diacetic acid tri(alkali metal) salt by alkaline hydrolysis of methylglycinediacetonitrile (MGDN), comprising the steps in the sequence (a) to (f):
(a) mixing of MGDN with aqueous alkali at a temperature of $\leq 30°$ C.;
(b) allowing the aqueous alkaline MGDN suspension to react at a temperature in the range from 10 to 30° C. over a period of from 0.1 to 10 h to form a solution;
(c) allowing the solution from step (b) to react at a temperature in the range from 30 to 40° C. over a period of from 0.1 to 10 h;
(d) optionally allowing the solution from step (c) to react at a temperature in the range from 50 to 80° C. over a period of from 0.5 to 2 h;
(e) optionally allowing the solution from step (c) or (d) to react at a temperature in the range from 110 to 200° C. over a period of from 5 to 60 min;
(f) hydrolysis and removal of ammonia of the solution obtained in step (c), (d) or (e) by stripping at a temperature of from 90 to 105° C.

8 Claims, No Drawings

METHOD FOR PRODUCING METHYLGLYCINE-N,N-DIETHANOIC ACID-TRIALKALI METAL SALTS WITH A LOW BY-PRODUCT CONTENT

The invention relates to a process for preparing low-by-product, light-color methylglycine-N,N-diacetic acid tri(alkali metal) salts by alkaline hydrolysis of methylglycine-N,N-diacetonitrile.

The aminopolyphosphonates, polycarboxylates or aminopolycarboxylates, such as ethylenediaminetetraacetic acid (EDTA), which are frequently used as complexing agents in detergents for example, are biodegradable only to a minor degree. An inexpensive alternative is provided by the glycine-N,N-diacetic acid derivatives, such as methylglycine-N,N-diacetic acid (MGDA) which is nontoxic and readily biodegradable. The use of MGDA and of related glycine-N,N-diacetic acid derivatives in detergents and their syntheses are described in WO-A 94/29421 and U.S. Pat. No. 5,849,950. For inexpensive production of the glycine-N,N-diacetic acid derivatives, high demands are made on the yield of the individual synthesis steps and purity of the isolated intermediates.

MGDA is prepared by reacting iminodiacetonitrile with acetaldehyde and hydrocyanic acid, or alpha-alaninenitrile with formaldehyde and hydrocyanic acid, and alkaline hydrolysis of the methylglycinediacetonitrile (MGDN) obtained as an intermediate with sodium hydroxide solution to obtain the trisodium salt of MGDA. In order to achieve high MGDA yields and purities, MDGA is isolated as an intermediate and used as a pure substance in the hydrolysis step which follows.

A problem in the hydrolysis of alkylglycinenitrile-N,N-diacetonitriles is their thermal lability, especially in an alkaline medium. The sterically demanding alkyl substitution promotes dissociation reactions. In the case of MGDN, primary dissociation products are in particular cyanide, acetaldehyde, iminodiacetonitrile (IDN) and formaldehyde. Under alkaline conditions, hydrolysis or other side reactions can additionally in particular give rise to the following by-products (in the form of sodium or potassium salts): iminodiacetate (IDA), nitrilotriacetate (NTA), carbonate, acetate, formate, glycolate, lactate, glycinate or alaninate. Cyanide is acutely toxic. NTA has been described as nephrotoxic. Cyanide and acetaldehyde tend to polymerize and can form colored by-products. Acetaldehyde can additionally, as a volatile component, contaminate the distillates of the co-product of the alkaline hydrolysis, ammonia.

U.S. Pat. No. 5,849,950 discloses the preparation of methylglycinediacetic acid by reacting alpha-alaninenitrile with formaldehyde and hydrocyanic acid, and alkaline hydrolysis of the methylglycinediacetonitrile (MGDN) formed as an intermediate with sodium hydroxide solution. For hydrolysis, crystalline MGDN is introduced at 40° C. into 20% by weight aqueous sodium hydroxide solution, stirred at 40° C. for 3 h and subsequently stirred further at 95° C. for another 5 h. In the hydrolysis, by-products are formed to a not inconsiderable degree, for example NTA.

It is an object of the invention to provide a process for preparing low-by-product, light-color methylglycine-N,N-diacetate.

The object is achieved by a process for preparing low-by-product, light-color methylglycine-N,N-diacetic acid tri(alkali metal) salt by alkaline hydrolysis of methylglycinediacetonitrile, comprising the steps in the sequence (a) to (f):

(a) mixing of methylglycinediacetonitrile (MGDN) with aqueous alkali at a temperature of $\leq 30°$ C.;

(b) allowing the aqueous alkaline MGDN suspension to react at a temperature in the range from 10 to 30° C. over a period of from 0.1 to 10 h to form a solution;

(c) allowing the solution from step (b) to react at a temperature in the range from 30 to 40° C. over a period of from 0.1 to 10 h;

(d) optionally allowing the solution from step (c) to react at a temperature in the range from 50 to 80° C. over a period of from 0.5 to 2 h;

(e) optionally allowing the solution from step (c) or (d) to react at a temperature in the range from 110 to 200° C. over a period of from 5 to 60 min;

(f) hydrolysis and removal of ammonia of the solution obtained in step (c), (d) or (e) by stripping at a temperature of from 90 to 105° C.

In a step (a), methylglycinediacetonitrile (MGDN) is mixed with aqueous alkali at a mixing temperature of $\leq 30°$ C. In general, the mixing temperature is from 10 to 30° C., preferably from 20 to 25° C. MGDN may be used as a solid, preferably as a powder, as a moist slurry or as an aqueous suspension. The aqueous alkali may be initially charged in a suitable mixing vessel (for example a stirred reactor) and MGDN may be metered in as a solid or aqueous suspension. Alkali and MGDN may also be metered in parallel into a mixing vessel or a tubular reactor. Useful aqueous alkali is aqueous NaOH (sodium hydroxide solution) or aqueous KOH (potassium hydroxide solution) having an alkali metal hydroxide content of generally from 5 to 50% by weight, preferably from 20 to 50% by weight. Preference is given to sodium hydroxide solution. The molar ratio of MGDN to alkali is generally 1:3.0-3.5, preferably 1:3.05-3.1.

Subsequently, the aqueous alkaline MGDN solution is allowed to react in steps (b) and (c), and two different temperature stages are passed through. First, the aqueous alkaline MGDN solution is allowed to react in a first stage (b) at a temperature in the range from 20 to 30° C., preferably from 25 to 30° C., over a period of from 0.1 to 10 h, preferably from 1 to 5 h, more preferably from 2 to 3 h, and subsequently, in a second stage (c), at a temperature in the range from 30 to 40° C., preferably from 35 to 40° C., over a period of from 0.1 to 10 h, preferably from 1 to 5 h, more preferably from 3 to 4 h.

In an optional step (d), the solution obtained in step (c) is allowed to react further at a temperature in the range from 50 to 80° C., preferably from 70 to 80° C., over a period of from 0.5 to 2 h, preferably from 1 to 2 h.

Step (c) or (d) may be followed by a so-called pressure hydrolysis as step (e). In this step, the solution obtained is hydrolyzed at a temperature in the range from 110 to 200° C., preferably from 140 to 180° C., over a period of from 5 to 60 min. In this step, the solution is under a pressure corresponding to the temperature ("autogenous").

Subsequently, in a step (f), ammonia is removed from the resulting solution by stripping at a temperature of from 90 to 105° C., preferably from 95 to 105° C. In the course of this, residual hydrolysis of the hydrolyzable components present in solution also takes place with formation of ammonia. For example, the solution is stripped substantially free of ammonia by pressure reduction to from 700 to 960 mbar. Preference is given to additionally using air as a stripping gas.

The solution obtained in step (f) may subsequently be substantially to fully depolarized by subjecting it to a bleaching step using hydrogen peroxide and/or activated carbon as the "bleach".

The inventive MGDN hydrolysis may be carried out batchwise, semicontinuously or continuously. The hydrolysis is carried out batchwise or semicontinuously, for example, in a stirred reactor; it is carried out continuously, for example, in a battery composed of stirred reactors and/or in tubular reactors and/or in loop reactors.

The technical-grade MGDA trisodium salt obtainable in accordance with the invention has a by-product content of generally <5% by weight based on the solid. The content of NTA trisodium salt is generally <0.3% by weight.

An aqueous crude product mixture comprising MGDN can be obtained by
1. Reacting iminodiacetonitrile (IDN) with HCN and acetaldehyde in aqueous solution. Iminodiacetonitrile can be obtained as an aqueous emulsion in a preceding stage from urotropin and hydrocyanic acid or from formaldehyde cyanohydrin and ammonia.
2. Reaction of alaninenitrile with HCN and formaldehyde in aqueous solution. Alaninenitrile may be obtained in a preceding stage from acetaldehyde, HCN and ammonia or acetaldehyde cyanohydrin and ammonia.

Preference is given to obtaining aqueous crude polymer mixture comprising MGDN as follows:

1a. Iminodiacetonitrile (IDN) is obtained by reacting urotropin, which can be obtained in situ from ammonia and formaldehyde, with hydrocyanic acid at a pH of from 5.5 to 6.3 and a temperature in the range from 20 to 90° C. The molar ammonia:formaldehyde:hydrocyanic acid ratio is generally 1:1.5, 1.5-1.9; the IDN concentration in the resulting aqueous emulsion is generally 15-40% by weight. Subsequently, the pH of the aqueous IDN emulsion is adjusted to 2-1.0 with mineral acid. The acidified IDN emulsion is then reacted with acetaldehyde and hydrocyanic acid to give MGDN. The molar IDN:acetaldehyde:HCN ratio is generally 1:1-1.2:1-1.2; the temperature in the reaction is generally 40-90° C. The MGDN concentration of the resulting aqueous emulsion is generally 20-50% by weight.

IDN can also be prepared by reacting formaldehyde cyanohydrin with ammonia. Alternatively, the starting reactant may be crystalline IDN which is suspended in water.

2a. Alpha-alaninenitrile (AN) is prepared by reacting excess ammonia with acetaldehyde and HCN or by reacting acetaldehyde cyanohydrin with excess ammonia, ammonia being usable in the form of an aqueous solution, in gaseous form or in liquid form. The reaction may be carried out under pressure. The excess ammonia is preferably distilled off under reduced pressure. The crude AN is reacted with formaldehyde and hydrocyanic acid to give MGDN. To this end, the pH of the aqueous AN solution is adjusted to 2-1.0 with mineral acid. The molar AN:formaldehyde:HCN ratio is generally 1:1.0-1.2:1.0-1.2; the temperature in the reaction is generally 40-90° C.

The MGDN concentration of the resulting aqueous emulsion is generally 20-50% by weight. MGDN can be removed from this by crystallization. To this end, the aqueous emulsion is preferably diluted to an MGDN content of 15-40% by weight with water before carrying out the crystallization.

It is also possible in accordance with the invention to hydrolyze the resulting aqueous crude mixture comprising MGDN under alkaline conditions. In this case too, the alkaline hydrolysis of the MGDN forms a smaller amount of by-products. However, this variant is less preferred owing to the considerable by-product content of the MGDN crude mixture. Preference is therefore given to initially removing MGDN from the crude mixture by crystallization and solid/liquid separation.

In a preferred embodiment of the crystallization, the crude product mixture which comprises MGDN and is generally present in the form of an emulsion of MGDN in a saturated aqueous MGDN solution is cooled below the solidification point only very slowly, i.e. with a small time-averaged cooling rate (expressed in K/h). Only when virtually the entirety of the emulsified MGDN has solidified is preference given to cooling with a greater cooling rate. The dissolved MGDN which then crystallizes out of the aqueous solution encounters already solidified, crystalline MGDN, as a result of which the new formation of crystal seeds is reduced or substantially entirely suppressed. Therefore, distinctly less or substantially no fines at all are formed. During the crystallization operation, water is evaporated, and this evaporation operation can be accompanied by a cooling and/or concentration of the mixture. The evaporation forms, adjoining the liquid/gas space interface of the aqueous mixture, a zone of supersaturation. In this zone of supersaturation, crystals can be formed and are then transported into the interior of the liquid and grow further there. Since, owing to the slow evaporation, new crystals are formed substantially below the liquid surface only in the very narrow zone of supersaturation and only these grow further in the interior of the liquid, fewer larger crystals are formed overall. Less mother liquor adheres to them; in particular, no mother liquor can be "incorporated" into agglomerates of ultrafine crystals, or the adhering mother liquor can be removed readily, for example by simple filtration or centrifugation. This considerably reduces the complexity of purification. This "vacuum cooling crystallization" also effectively prevents encrustation of the walls of the crystallizer.

The aqueous mixture comprising MGDN may be cooled by evaporation of water, in the course of which the MGDN concentration of the mixture is kept substantially constant. This variant may also be referred to as "vacuum cooling crystallization" which is carried out with total reflux. The aqueous mixture may be concentrated by evaporating water, in the course of which the temperature of the mixture is kept substantially constant. This variant may also be referred to as "isothermal evaporative crystallization". Both operations, i.e. both cooling and concentration of the aqueous mixture, may also be effected successively or simultaneously.

At a certain temperature of the aqueous mixture, generally below about 30° C., the heat can no longer be removed by evaporative cooling alone owing to the water vapor pressure which is then low, but rather via the vessel walls of the crystallizer, preferably by brine cooling.

The crystallizer may be of any design. It may, for example, be a stirred tank crystallizer, forced circulation crystallizer, guide tube crystallizer or fluidized bed crystallizer, for example of the Oslo type.

The invention is illustrated in detail by the examples which follow.

EXAMPLES

Comparative Example 1

148 g (1.0 mol) of pure MGDN are introduced at approx. 80° C. with vigorous stirring into 608 g (3.04 mol) of 20% by weight sodium hydroxide solution within approx. 2 h. Subsequently, the mixture is stirred further at 80° C. for 3 h under nitrogen. Afterward, the mixture is stripped with nitrogen at 95° C. for approx. 5 h. During this, the solids concentration is kept below 45% by weight by adding water. This results in a dark brown solution (Hazen color number>1000) with the following composition: MGDA-$Na_3$: 230 g (0.85 mol, yield=85%), corresponding to 657 g of an approx. 35% by weight MGDA-$Na_3$ solution; NTA-$Na_3$: 1.9% by weight; IDA-$Na_3$: 3.7% by weight; $Na_2CO_3$: 1.5% by weight; NaOH: 0.2% by weight; Na acetate: 0.4% by weight; Na formate:

0.3% by weight; Na glycolate: 0.5% by weight; Na lactate: 0.4% by weight; Na glycinate: 0.2% by weight; Na alaninate: 0.3% by weight; acetaldehyde: 1.5% by weight; water: 55% by weight.

Comparative Example 2

148 g (1.0 mol) of pure MGDN are introduced at approx. 40° C. with vigorous stirring into 608 g (3.04 mol) of 20% by weight sodium hydroxide solution within approx. 2 h. Subsequently, the mixture is stirred further at 40° C. for 3 h under nitrogen. Afterward, the mixture is stripped with nitrogen at 95° C. for approx. 5 h. During this, the solids concentration is kept below 45% by weight by adding water. This results in a brown solution (Hazen color number: 445) with the following composition: MGDA-$Na_3$: 247 g (0.91 mol, yield=91%), corresponding to 705 g of an approx. 35% MGDA-$Na_3$ solution; NTA-$Na_3$: 0.3% by weight; IDA-$Na_2$: 2.5% by weight; $Na_2CO_3$: 0.3% by weight; NaOH: 0.3% by weight; Na acetate: 0.2% by weight; Na formate: 0.15% by weight; Na glycolate: 0.2% by weight; Na lactate: 0.1% by weight; Na glycinate: 0.1% by weight; Na alaninate: 0.1% by weight; acetaldehyde: 720 ppm; water: 60% by weight.

Example 1

148 g (1.0 mol) of pure MGDN are introduced at approx. 25° C. with vigorous stirring into 608 g (3.04 mol) of 20% by weight sodium hydroxide solution within approx. 2 h. Subsequently, the mixture is stirred further under nitrogen first at 30° C. for 3 h and then at 40° C. for 2 h. Afterward, the mixture is stripped with nitrogen at 95° C. for approx. 5 h. During this, the solids concentration is kept below 45% by weight by adding water. This results in a yellow-orange solution (Hazen color number: 95) with the following composition: MGDA-$Na_3$: 260 g (0.96 mol, yield=96%), corresponding to 650 g of an approx. 40% by weight MGDA-$Na_3$ solution; NTA-$Na_3$: <0.1% by weight; IDA-$Na_2$: 0.8% by weight; $Na_2CO_3$: 0.1% by weight; NaOH: 0.2% by weight; Na acetate: 0.6% by weight; Na formate: 0.07% by weight; Na glycolate: 0.07% by weight; Na lactate: 0.0% by weight; Na glycinate: 0.06% by weight; Na alaninate: 0.1% by weight; acetaldehyde: 80 ppm; water: 55% by weight.

Example 2

148 g (1.0 mol) of pure MGDN are introduced at approx. 25° C. with vigorous stirring into 608 g (3.04 mol) of 20% by weight sodium hydroxide solution within approx. 2 h. Subsequently, the mixture is stirred further under nitrogen first at 30° C. for 3 h and then at 40° C. for 2 h. In contrast to example 1, the mixture is now heated to 170° C. in a tubular reactor under pressure for 15 minutes. Afterward, the mixture is stripped with nitrogen at 100-104° C. within approx. 5 h. During this, the solids concentration is kept below 45% by weight by adding water. This results in a yellow-orange solution (Hazen color number: 105) with the following composition: MGDA-$Na_3$: 257 g (0.95 mol, yield=95%), corresponding to 643 g of a 40% by weight MGDA-$Na_3$ solution; acetaldehyde: <10 ppm.

What is claimed is:

1. A process for preparing low-by-product, light-color methylglycine-N,N-diacetic acid tri(alkali metal) salt by alkaline hydrolysis of methylglycinenitrilediacetonitrile (MGDN), comprising the steps in the sequence (a) to (f):
   (a) mixing of MGDN with aqueous alkali at a temperature of $\leq 30°$ C.
   (b) allowing the aqueous alkaline MGDN suspension to react at a temperature in the range from 25 to 30° C. over a period of from 1 to 5 h to form a solution;
   (c) allowing the solution from step (b) to react at a temperature in the range from more than 30 to 40° C. over a period of from 1 to 5 h;
   (d) optionally allowing the solution from step (c) to react at a temperature in the range from 50 to 80° C. over a period of from 0.5 to 2 h;
   (e) optionally allowing the solution from step (c) or (d) to react at a temperature in the range from 110 to 200° C. over a period of from 5 to 60 min;
   (f) hydrolysis and removal of ammonia of the solution obtained in step (c), (d) or (e) by stripping at a temperature of from 90 to 105° C.

2. The process according to claim 1, wherein the temperature in step (b) is from 25 to 30° C. and the temperature in step (c) is from 35 to 40° C.

3. The process according to claim 1, wherein the aqueous alkali used is from 5 to 50% by weight sodium hydroxide solution.

4. The process according to claim 1, which is carried out batchwise, semicontinuously or continuously.

5. The process according to claim 1, which is carried out continuously.

6. The process according to claim 1, wherein in step (a) a molar ratio of MGDN to alkali ranges from 1:3.0 to 1:3.5.

7. The process according to claim 1, wherein (d) the solution from step (c) is allowed to react at a temperature in the range from 50 to 80° C. over a period of from 0.5 to 2 h.

8. The process according to claim 1, wherein (e) the solution from step (c) or (d) is allowed to react at a temperature in the range from 110 to 200° C. over a period of from 5 to 60 min.

* * * * *